(12) United States Patent
Randol et al.

(10) Patent No.: US 8,157,846 B2
(45) Date of Patent: Apr. 17, 2012

(54) LOCKING MECHANISM WITH TWO-PIECE WASHER

(75) Inventors: David S. Randol, Odessa, FL (US); David A. Walsh, Reading, MA (US)

(73) Assignee: Ingenium S.A., Panama (PA)

( * ) Notice: Subject to any disclaimer, the term of this patent is extended or adjusted under 35 U.S.C. 154(b) by 936 days.

(21) Appl. No.: 12/179,136

(22) Filed: Jul. 24, 2008

(65) Prior Publication Data

US 2010/0023061 A1     Jan. 28, 2010

(51) Int. Cl.
*A61B 17/70* (2006.01)
(52) U.S. Cl. ........................ 606/279; 606/268
(58) Field of Classification Search .................. 606/246, 606/250, 257, 259, 261, 264–268, 270, 272, 606/273, 278, 279, 301, 305, 308; 403/150, 403/362; 411/393
See application file for complete search history.

(56) References Cited

U.S. PATENT DOCUMENTS

| | | | |
|---|---|---|---|
| 4,763,644 A | 8/1988 | Webb |
| 4,805,602 A | 2/1989 | Puno et al. |
| 4,887,596 A | 12/1989 | Sherman |
| 4,946,458 A | 8/1990 | Harms et al. |
| 5,154,718 A | 10/1992 | Cozad et al. |
| 5,549,608 A | 8/1996 | Errico et al. |
| 5,647,873 A | 7/1997 | Errico et al. |
| 5,672,176 A | 9/1997 | Biedermann et al. |
| 5,713,898 A | 2/1998 | Stucker et al. |
| 5,738,685 A | 4/1998 | Halm et al. |
| 5,749,916 A | 5/1998 | Richelsoph |
| 5,863,293 A | 1/1999 | Richelsoph |
| 5,879,350 A | 3/1999 | Sherman et al. |
| 5,882,350 A | 3/1999 | Ralph et al. |
| 5,961,516 A | 10/1999 | Graf |
| 5,964,760 A | 10/1999 | Richelsoph |
| 5,976,187 A | 11/1999 | Richelsoph |
| 5,989,250 A | 11/1999 | Wagner et al. |
| 6,010,503 A | 1/2000 | Richelsoph et al. |
| 6,017,345 A | 1/2000 | Richelsoph |
| 6,053,917 A | 4/2000 | Sherman et al. |
| 6,063,090 A | 5/2000 | Schlapfer |
| 6,090,111 A | 7/2000 | Nichols |
| 6,132,432 A | 10/2000 | Richelsoph |
| 6,248,105 B1 | 6/2001 | Schlapfer et al. |
| 6,273,889 B1 | 8/2001 | Richelsoph |
| 6,287,311 B1 | 9/2001 | Sherman et al. |
| 6,328,740 B1 | 12/2001 | Richelsoph |
| 6,355,040 B1 | 3/2002 | Richelsoph et al. |
| RE37,665 E | 4/2002 | Ralph et al. |
| 6,371,957 B1 | 4/2002 | Amrein et al. |
| 6,485,492 B1 | 11/2002 | Halm et al. |
| 6,565,565 B1 | 5/2003 | Yuan et al. |

(Continued)

FOREIGN PATENT DOCUMENTS

CA     2133484     1/1995

(Continued)

*Primary Examiner* — Eduardo C Robert
*Assistant Examiner* — David Comstock
(74) *Attorney, Agent, or Firm* — Renner, Otto, Boisselle & Sklar, LLP (57) ABSTRACT

Locking mechanisms and methods of fixation, such as the fixation of a fixation device like a bone screw and of a rod to the spine. The locking mechanism includes a body, a rod seat and a set screw. The rod seat is configured to separate into two pieces when the rod exerts force on the top portion of the washer and the set screw limits movement of the washer toward the bottom of the locking mechanism.

9 Claims, 9 Drawing Sheets

U.S. PATENT DOCUMENTS

| | | |
|---|---|---|
| 6,733,502 B2 | 5/2004 | Altarac et al. |
| 6,740,086 B2 | 5/2004 | Richelsoph |
| 6,905,500 B2 | 6/2005 | Jeon et al. |
| 2003/0125742 A1 | 7/2003 | Yuan et al. |
| 2005/0203516 A1 | 9/2005 | Biedermann et al. |
| 2005/0216003 A1 | 9/2005 | Biedermann et al. |
| 2005/0277928 A1 | 12/2005 | Boschert |
| 2006/0106383 A1 | 5/2006 | Biedermann et al. |
| 2007/0049933 A1 | 3/2007 | Ahn et al. |
| 2007/0073291 A1 | 3/2007 | Cordaro et al. |
| 2007/0118123 A1 | 5/2007 | Strausbaugh et al. |
| 2007/0270839 A1 | 11/2007 | Jeon et al. |

FOREIGN PATENT DOCUMENTS

| | | |
|---|---|---|
| EP | 1 570 794 | 9/2005 |
| WO | 98/27884 | 7/1998 |
| WO | 02/054966 A2 | 7/2002 |
| WO | 03/037199 A1 | 5/2003 |
| WO | 2006116437 | 11/2006 |

LOCKING MECHANISM WITH TWO-PIECE WASHER

FIELD OF THE INVENTION

The present invention relates generally to prostheses for treating spinal pathologies, and more specifically to spinal fixation assemblies including an anchor for holding a fixation device and a stabilization rod.

BACKGROUND OF THE INVENTION

Various methods of spinal immobilization have been used in the treatment of spinal instability and displacement. The most common treatment for spinal stabilization is immobilization of the joint by surgical fusion, or arthrodesis. This has been known for almost a century. In many cases, however, pseudoarthrosis occurs, particularly in cases involving fusion across the lumbosacral articulation and when more than two vertebrae are fused together. Early in the century, post operative external immobilization, such as through the use of splints and casts, was the favored method of spinal fixation. As surgical techniques became more sophisticated, various new methods of internal and external fixation were developed.

Internal fixation refers to therapeutic methods of stabilization that are wholly internal to the patient and include commonly known devices such as bone plates, screws, rods and pins. External fixation, in contrast, involves at least some portion of the stabilization device being located external to the patients' body. As surgical technologies and procedures became more advanced and the likelihood of infection decreased, internal fixation eventually became the favored method of immobilization since it is less restrictive on the patient.

Internal fixation of the spine may be used to treat a variety of disorders including kyphosis, spondylolisthesis and rotation, segmental instability, such as disc degeneration and/or fracture caused by disease, trauma, congenital defects and tumor diseases. One of the main challenges associated with internal spinal fixation is securing the fixation device to the spine without damaging the spinal cord. The pedicles of a vertebra are commonly used for fixation as they generally offer an area that is strong enough to hold the fixation device in place even when the patient suffers from degenerative instability such as osteoporosis.

Current fixation devices and hardware systems used internally for spinal fixation in modern surgical procedures are generally designed to meet one or more criteria, such as: providing rigidity as is indicated, generally along the long axis of the patient's spine; accommodating a broad variation in the size and shape of the spinal member with which it is used; having the capability of handling the stresses and strains to which the devices will be subjected resulting from movement of the spine; and providing easy surgical access during both implantation and removal of the implant.

The present invention includes novel fixation devices and methods of fixation the relative positions of a rod and fixation device.

BRIEF SUMMARY OF THE INVENTION

According to an aspect of the invention, a locking mechanism includes a body having a bottom portion and a side portion, the side portion being configured to receive a rod; a fixation device extending at least partially through a hole in the bottom portion of the body; and a rod seat between the rod and the fixation device, the rod seat having a top portion configured to interact with the rod and a bottom portion configured to receive part of the fixation device; wherein the rod seat is configured to separate into two pieces when the rod exerts force on the top portion of the rod seat and the fixation device limits movement of the rod seat toward the bottom portion of the body.

The locking mechanism may further include a locking element on the side of the rod opposite the rod seat, wherein engaging the locking element causes the locking element to exert force on the rod and further causes the rod to exert force on the rod seat. In addition, the amount of force exerted on the rod by the locking element sufficient to cause the rod seat to separate into two pieces may range from approximately 50 lbs to approximately 2500 lbs.

The top portion of the rod seat may include a taper and wherein the force exerted by the rod on the top portion of the rod seat causes the taper to widen. Moreover, the rod seat may be thinnest from top to bottom at approximately the midline of the taper.

The rod seat also may be configured to separate at a predetermined location, which may be located approximately at a central axis of the rod seat and approximately parallel to a major axis of the rod. In addition, the predetermined location may mechanically weakened compared to the remainder of the rod seat, such as by being thinned, notched, grooved, scored or perforated.

Once separated, the pieces of the rod seat of the locking mechanism may be substantially mirror images of one another. In addition, the two pieces of the rod seat may each be configured to exert force on the fixation device directed at an angle that is off axis from the central axis of the body by up to approximately 45 degrees. In one embodiment, the angle ranges from about 10 degrees to about 30 degrees.

Also according to an aspect of the invention, the bottom portion of the rod seat may include at least two internal steps, each having an edge configured to engage the fixation device. At least one of the steps may be noncontinuous. In addition, the edge of one of the internal steps may define an opening in the bottom portion of the rod seat.

Also according to an aspect of the invention, the bottom portion of the body may include at least one lip configured to engage the fixation device, which may be noncontinuous.

According to another aspect of the invention, a method for locking the relative positions of a fixation device and a rod includes placing a fixation device through a hole in the top of a body of the locking mechanism; placing a rod seat having a top portion and a bottom portion through the hole in the top portion of a body of a locking mechanism, wherein the rod seat is configured to separate into two pieces when force is applied to the top portion of the rod seat and movement of the rod seat is restricted; placing a rod in a side portion of the body such that the rod and the fixation device are on opposite sides of the rod seat; and urging the rod toward the bottom of the body such that the rod applies force to the top portion of the rod seat and the fixation device restricts movement of the rod seat toward the bottom of the body, thereby causing the rod seat to separate into two pieces; wherein each of the two pieces engage part of the fixation device.

The method may further include further urging the rod toward the bottom of the body following the separation of the rod seat into two pieces, which may result in increasing the engagement between the pieces of the rod seat and the fixation device. In addition, the ability of the locking mechanism to maintain the rod and fixation mechanism in locked positions may be enhanced following the separation of the rod seat and further urging of the rod toward the bottom of the body.

In addition, urging the rod toward the bottom of the body may include engaging a locking element on the side of the rod opposite the rod seat. Urging the rod toward the bottom of the body may also include exerting from approximately 50 lbs to approximately 2500 lbs of force on the rod.

Also according to an aspect of the invention, at least one lip at a bottom portion of the body may restrict the movement of the fixation device toward the bottom of the body, thereby restricting the movement of the rod seat toward the bottom of the body during the application of force by the rod to the top portion of the rod seat.

According to another aspect of the invention, a rod seat for use in a locking mechanism configured to lock the relative positions of a rod and a fixation device includes a top portion having a taper configured to receive part of the rod; a bottom portion configured to receive part of the fixation device; wherein the rod seat is configured to separate into two pieces when the rod exerts from approximately 50 lbs to approximately 2500 lbs of force on the top portion of the rod seat and the fixation device limits movement of the rod seat away from the rod; and wherein locking of the relative positions of the rod and the fixation device is enhanced following the separation of the rod seat into two pieces.

The two pieces of the rod seat may each be configured to exert force on the fixation device directed at an angle that is off axis from the central axis of the body by up to approximately 45 degrees. In one embodiment, the angle ranges from about 10 degrees to about 30 degrees.

The features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

DETAILED DESCRIPTION OF THE INVENTION

The invention relates to novel locking mechanisms and methods for locking the relative positions of a rod and a fixation device. The locking mechanisms provide improved locking between a rod and the head of a fixation device, such as a screw. The various locking mechanisms disclosed herein include either a rod seat or a washer disposed between the rod and the fixation device.

Figure 1:
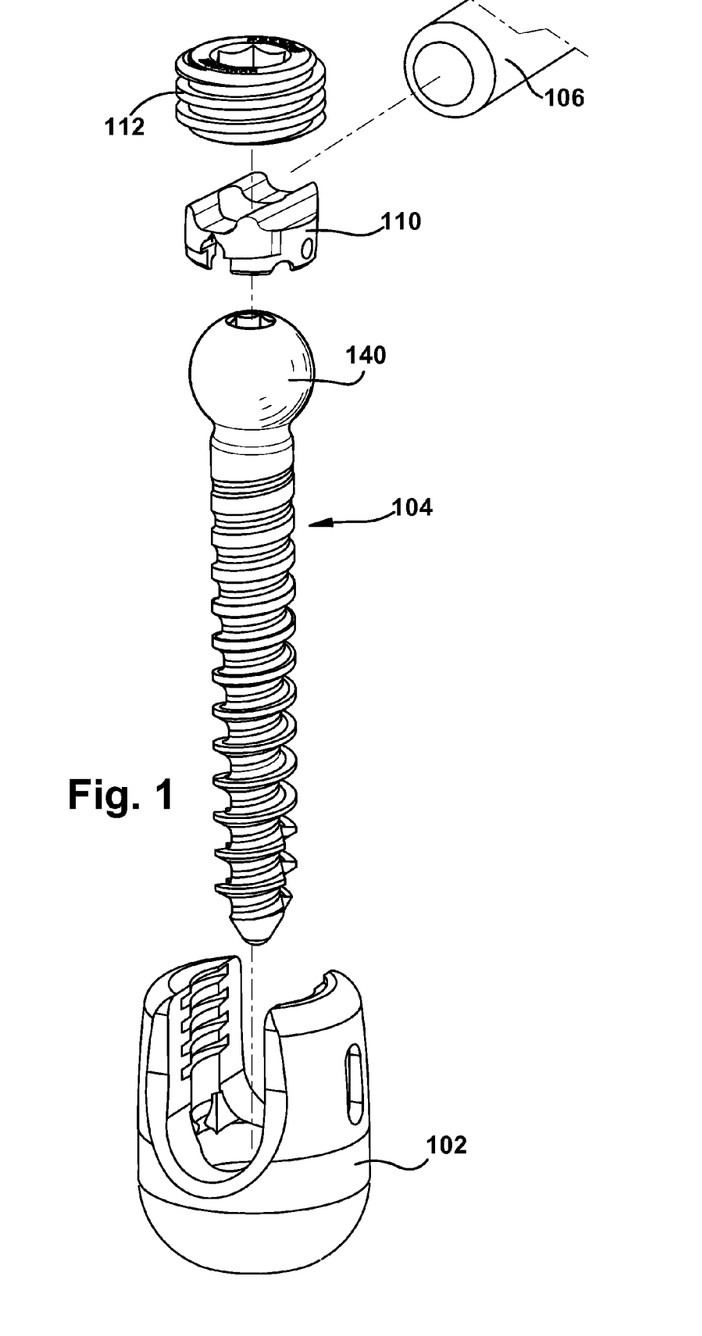
FIG. 1 is an exploded perspective view of a locking mechanism with a fixation device and a rod.
Figure 2A:
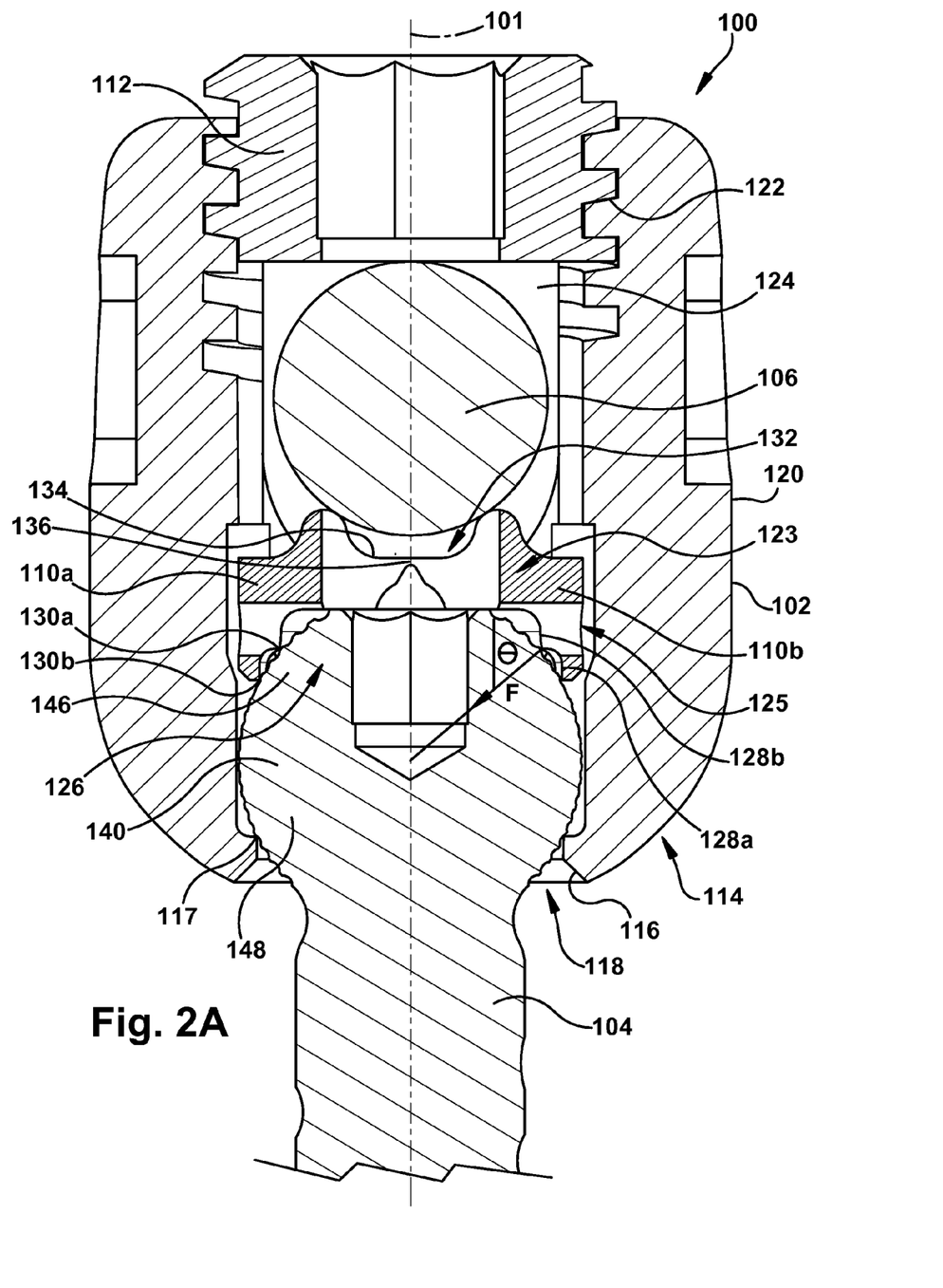
FIG. 2A is a cross-sectional view of the locking mechanism of FIG. 1 in an unlocked position.
Figure 2B:
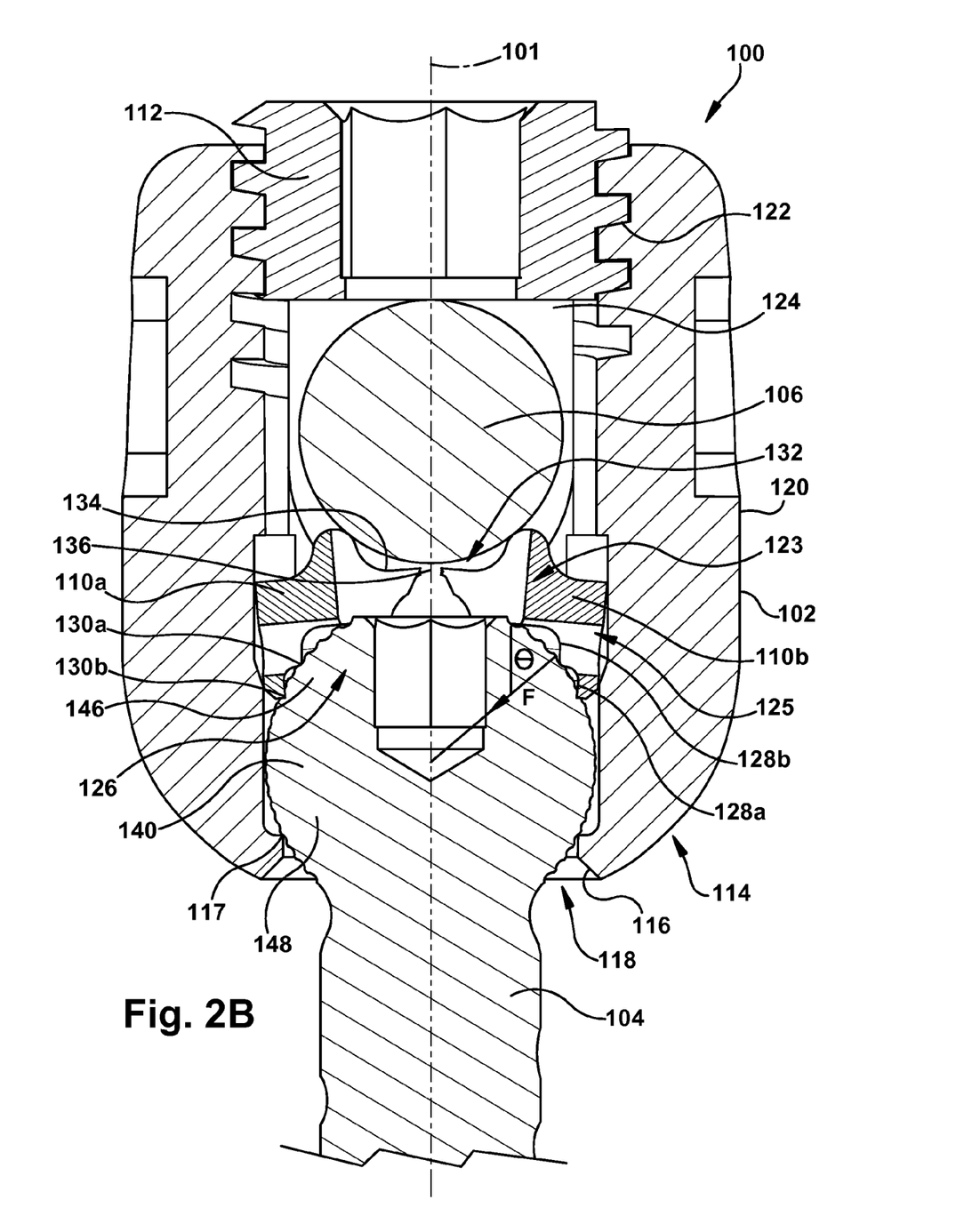
FIG. 2B is a cross-sectional view of the locking mechanism of FIGS. 1 and 2A in a locked position.

Turning initially to FIGS. 1 and 2A-B, FIG. 1 shows an exploded perspective view of a locking mechanism, and FIGS. 2A-B show cross sectional views of the locking mechanism of FIG. 1 in unlocked and locked positions. The locking mechanism 100 is configured to engage and lock the position of a fixation device 104 with respect to the position of a rod 106. The locking mechanism 100 includes a body 102, a rod seat 110, and a locking element 112.

When the locking mechanisms of the present invention are used for spinal fixation, "above" or "top" means posterior with respect to the patient and "below" or "bottom" means anterior with respect to the patient. Thus, the bottom portion 114 of the body 102 is anterior with respect to the patient and the rod 106 is received by the body 102 as the rod 106 is moved in a posterior to anterior direction.

The body 102 includes a bottom portion 114 that includes a hole 118. The fixation device 104 passes partially through the hole 118. Preferably, the hole 118 is large enough to allow the shaft 142 of the fixation device 104 to pass through but not large enough to allow the bottom portion 148 of the head 140 of the fixation device 104 to pass through. Thus, the hole 118 is preferably dimensioned to prevent the fixation device 104 from exiting the body 102.

The fixation device 104 is preferably inserted through the top of the body 102 prior to insertion of the rod seat 110 and rod 106. The rod seat 110 is then preferably inserted through the top of the body 102 so that the bottom portion 125 of the rod seat 110 is positioned for interaction with the top portion 146 of the head 140 of the fixation device. As will be understood by those skilled in the art, the rod seat 110 may be wider than the opening in the top of the body 102. In such an embodiment, a tool may be used to increase the size of the opening in the top of the body 102 prior to inserting the rod seat 110.

The body 102 also includes a side portion 120 that is configured to receive the rod 106, such as by way of a channel 124 that enables placement of the rod 106 by either sliding the rod 106 through the side portion 120 of the body or by inserting the rod 106 into the channel 124 through the top portion of the body 102. The rod seat 110 is preferably inserted into the body 102 prior to insertion of the rod 106 such that the rod seat 110 is eventually positioned between the rod 106 and the head 140 of the fixation device 104.

The locking mechanism 100 may also include a locking element 112 that is configured to engage the body 102 and the rod 106 so as to force the rod 106 toward the fixation device 104. The locking element 112 and body 102 may be, for example, slidably engageable, rotatably engageable and/or snapably engageable. Accordingly, the body 102 may include threads 122 for engaging the locking element 112. In addition, while FIGS. 1, 2A-B and 4 show internal threads, it will be understood by those of ordinary skill in the art that the threads may also be external threads and the locking element 112 may surround the body 102 during engagement. Preferably, the locking element 112 is a set screw, which may be either internally or externally threaded to engage either an externally or internally threaded body 102.

Each of the body 102, the rod seat 110, the locking element 112, the fixation device 104 and the rod 106 may be made from a variety of materials known in the art and preferably is made from a biocompatible material when the locking mechanism 100 is used for bone fixation. Such materials include, but are not limited to, titanium, titanium alloys (e.g. titanium/aluminum/vanadium (Ti/Al/V) alloys), cobalt-chromium alloys, stainless steel, ceramics (alumina ceramic, zirconia ceramic, yttria zirconia ceramic, etc.), high strength polymers (e.g. PEEK, PEKK, etc.), pyrolytic carbon, tantalum, carbon composite materials and combinations thereof, which may include mechanically compatible mixtures of the above materials. Such materials are commonly used in bone fixation and the like. Preferably, the materials are rigid and in one embodiment, the body 102, fixation device 104, rod 106, rod seat 110 and locking element 112 are all made from Ti/Al/V alloys, such as Ti/6Al/4V ELI.

While one of skill in the art will recognize that fixation devices 104 other than a screw can be used without departing from the scope of the present invention, a screw is shown and described to illustrate the engagement of the fixation device 104 and the body 102, as well as the method for locking the relative positions of a fixation device 104 and a rod 106. Furthermore, various types of screws may be used. Preferably, however, the fixation device 104 has an at least partially spherical head 140.

The size of the body 102 may be similar to that of known devices. For example, the height of body 102 may range from about 0.4 inch to about 1 inch. Also, the width of body 102 may range from about 0.25 inch to about 1 inch.

The bottom portion 114 of the body 102 may be tapered and may have a socket 116 and a hole 118. Because the general shape of the type of body 102 illustrated in FIGS. 1, 2A-B and 4 somewhat resembles a tulip flower, the type of body 102 is often referred to as a "tulip" by those skilled in the art. The socket 116 is preferably sized to accept the head 140 of the fixation device 104, such as a screw. The hole 118 is preferably located at the bottom portion 114 of the body 102.

Turning next to FIGS. 3A-D, various views of an embodiment of the rod seat 110 of the present invention are illustrated. The rod seat 110 has a top portion 123 for interacting with the rod 106 and a bottom portion 125 for interacting with the fixation device 104. The rod seat 110 may be configured to at least partially surround the head 140 of the fixation device 104. The rod seat 110 may also include a top hole 132 and a bottom hole 126 to provide access to the head 140 of the fixation device 104 from the top of the body 102. Thus, a driver or similar device may be used to engage the head 140 of the fixation device 104 via the rod seat 110. In this manner, the fixation device 104 can be tightened using a driver or the like without fixing the position of the fixation device 104 with respect to the body 102 and rod 106.

The rod seat 110 may serve multiple functions, such as aiding in the alignment of the rod 106, creating a contact surface for the rod 106, exerting forces on the head 140 that have both vertical and lateral components, and preventing linear compressive forces from being transferred from the rod 106 to the top of the head 140.

In addition, the rod seat 110 also preferably includes a taper 134 for receiving the rod 106. Preferably, the midline of the taper 134 is aligned with the central axis 101 of the body 102 to facilitate alignment of the rod 106 within the body 102. In this manner, the taper 134 facilitates placement of the rod 106 within the body 102 such that the center of the rod 106 is generally aligned with the central axis 101 of the body 102.

Moreover, the rod seat 110 may also be wider lengthwise than widthwise, or wider widthwise than lengthwise, to cause the rod seat 106 to resist rotation inside the body 102, which in turn may facilitate alignment of the rod 106 within the body 102.

In addition, the taper 134 may include multiple curved surfaces on each side of the rod seat 110. The multiple curved surfaces may create engagement surfaces for rods of varying diameter. For example, the rod seat 110 may be configured to engage rods ranging from about 3 mm to about 7 mm in diameter. The diameter of the rod 106 may determine which of the curved surfaces of the taper 134 contacts the rod 106. In addition, a rod 106 may also contact the taper 134 such that the rod 106 is in contact with more than curved surface.

The rod seat 110 includes a bottom hole 126 that is sized to accept part of the top portion 146 of the head 140 of the fixation device 104. The rod seat 110 may also include internal steps 128a and 128b. The internal steps 128a and 128b each have an edge 130a and 130b, respectively for contacting the surface of the top portion 146 of the head 140 of the fixation mechanism 104 during engagement. In addition, the edge 130a may define the opening 126 of the rod seat 110 and both edge 130a and edge 130b may define generally circular openings.

The body 102 includes a channel 124 in the side portion 120 for receiving the rod 106 or other stabilization element, such as a dynamic stabilization element. While a channel 124 is preferred for receiving the rod 106, it will be understood by those skilled in the art that an aperture in the side portion 120 could also receive the rod 106, though a body 102 with an aperture may be more cumbersome to deploy during surgery as a surgeon would have to place the rod 106 through the aperture instead of placing the rod 106 in the channel 124. Using a channel 124 to receive the rod 106 may provide greater flexibility for a surgeon.

It is desirable to retain the rod 106 within the channel 124 after placement. Accordingly, the side portion 120 of the body 102 also includes threads 122 configured to engage locking element 112, which is preferably a set screw. Although internal threads 122 are illustrated, the threads 122 may be either internal or external to the body 102 depending on the configuration of the body 102 and the locking element 112.

The locking element 112 is thus engaged with the threads 122 of the side portion 120 of the body 102 to keep the rod 106 within the channel 124. It should be understood, however, that the locking element 112 need not engage the body 102 via threaded engagement. The locking element 112 and the body 102 may be slidably engageable, rotatably engageable, and/or snapably engageable. In the embodiments disclosed in FIGS. 1, 2A-B and 4, the locking element 112 and the body 102 are rotatably engageable. To fix the rod 106 with respect to the fixation device 104, the locking element 112 preferably is tightened down to apply force to the rod 106 in order to engage and lock the rod 106 and fixation device 104.

More specifically, the tightening of the locking element 112 causes linear compression of the locking element 112 onto the rod 106, which in turn causes the rod 106 to exert force on the top portion 123 of the rod seat 110, which in turn forces the fixation device 104 toward the bottom portion 114 of the body 102. Thus, as the rod 106 is forced downward, such as by tightening of the locking element 112, the rod seat 110 and head 140 combination is forced downward into the socket 116, which preferably includes a lip 117. As shown, the lip 117 is tapered and preferably has an edge. Moreover, the lip 117 may be noncontinuous around the perimeter of the body 102 such that only portions of the perimeter of the body 102 include the lip 117.

Accordingly, the lower portion 148 of the head 140 is caused to contact the lip 117, and preferably, the edge of the lip, thereby preventing the head 140 of the fixation device 104 from moving through the hole 118. As the locking element 112 is further tightened, the rod 106 is forced more tightly against the top portion 123 of the rod seat 110. At the same time, the lip 117 prevents further movement of the fixation device 104 toward the bottom 114 of the body 102. Accordingly, the fixation device 104 limits movement of the rod seat 110 toward the bottom portion 114 of the body 112.

The socket 116 is configured for locking engagement of the fixation device 104. In order to facilitate locking engagement, the surface of the socket 116 may include a rough or knurled surface and/or a surface fixation mechanism, such as ridges, grooves, bumps, pips, or the like to increase the coefficient of friction of the surface. In addition, the head 140 may have rough or knurled surfaces and/or surface fixation mechanisms, such as ridges, grooves, bumps, pips, or the like to increase the coefficient of friction of the surfaces. For example, the surfaces may roughened by blasting, for example, with titanium oxide, glass beads or other suitable blasting material. One of skill in the art will understand that other surface treatments may also be used on the surfaces of the socket 116 and the head 140.

Referring to FIGS. 2A-B and 3A-D, the rod seat 110 is preferably configured to separate into two pieces 110a and 110b when the rod 106 exerts force on the top portion 123 of the rod seat 110 and the fixation device 104 restricts movement of the rod seat 110 toward the bottom portion 114 of the body 112. The two pieces 110a and 110b of the rod seat 110 may be substantially mirror images of each other. For example, piece 110b may be substantially a mirror image of piece 110a. The force exerted on the rod seat 110 by the rod 106 sufficient to cause the rod seat 110 to separate into two pieces 110a and 110b may range from approximately 50 lbs to approximately 2500 lbs. The rod seat 110 may also be configured to separate at a predetermined location, such as location 136. In one embodiment, the predetermined location 136 is approximately at a central axis of the rod seat 110 and parallel to a major axis of the rod 106. To facilitate separation, the predetermined location 136 of the rod seat 110 may be mechanically weakened compared to the remainder of the rod seat 110. For example, the predetermined location 136 may be at least one of: thinned, grooved, scored or perforated.

In addition, the top portion 123 of the rod seat 110 may include a taper 132 for receiving the rod 106. The taper 132 may function to center the rod 106 with respect to the rod seat 110 or body 102. Preferably, the midline of the taper 132 is approximately at a central axis of the rod seat 110 and parallel to a major axis of the rod 106, which may be the site of the predetermined location 136. As such, the rod seat 110 may be thinnest from top to bottom at approximately the center of the taper 132.

The taper 132 may also facilitate separation of the rod seat 110 into two pieces 110a and 110b because the rod 106 causes the taper 132 to widen as the rod 106 is forced down on the top portion 123 of the rod seat 110 and into the taper 132. For example, the force that is applied by the rod 106 to the top portion 123 of the rod seat 110 may have a resultant force on each side of the tape 132 of the rod seat 110 that has a downward and an outward component. Thus, when the rod seat 110 separates into two pieces 110a and 110b, further urging of the rod 106 toward the bottom portion 114 of the body 102 causes the pieces 110a and 110b to further separate and move outward toward the until the movement of the pieces 110a and 110b is restricted by the side of the body 102. The further urging of the rod 106 may increase the engagement between the fixation device 104 and the pieces 110a and 110b of the rod seat 110. In addition, the pieces 110a and 110b may impact a downwardly tapered inner wall section of the body 102 such that the pieces 110a and 110b are directed toward the head 140 of the fixation device 104 at an angle offset from the major axis 101 of the body 102, such as angle θ.

Figure 3A:
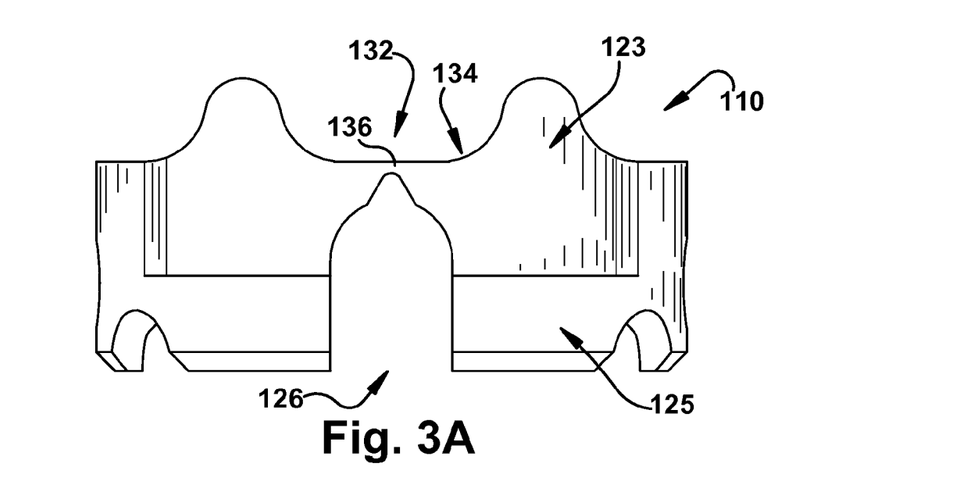
FIGS. 3A-D are views of the rod seat of the locking mechanism of FIGS. 1 and 2A-B.
Figure 3B:
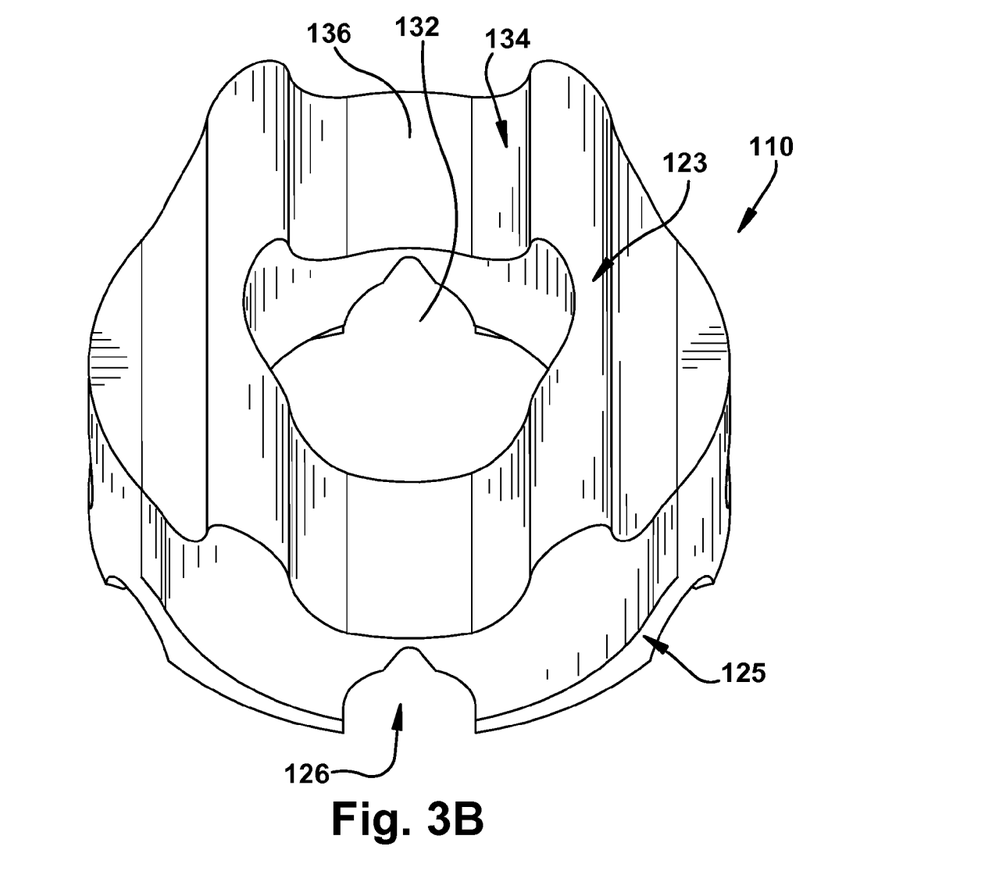
Figure 3C:
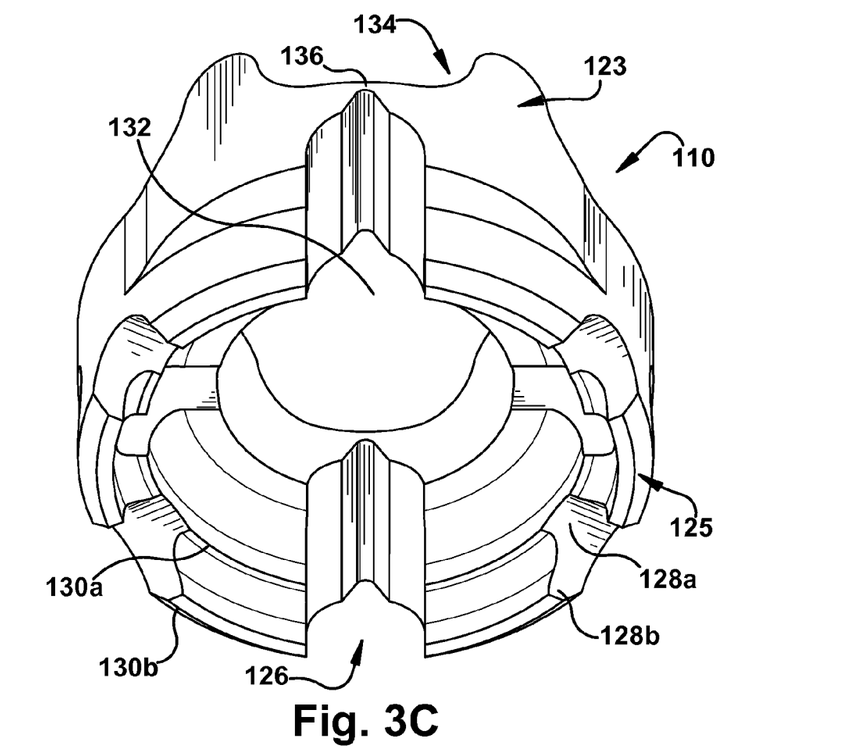
Figure 3D:
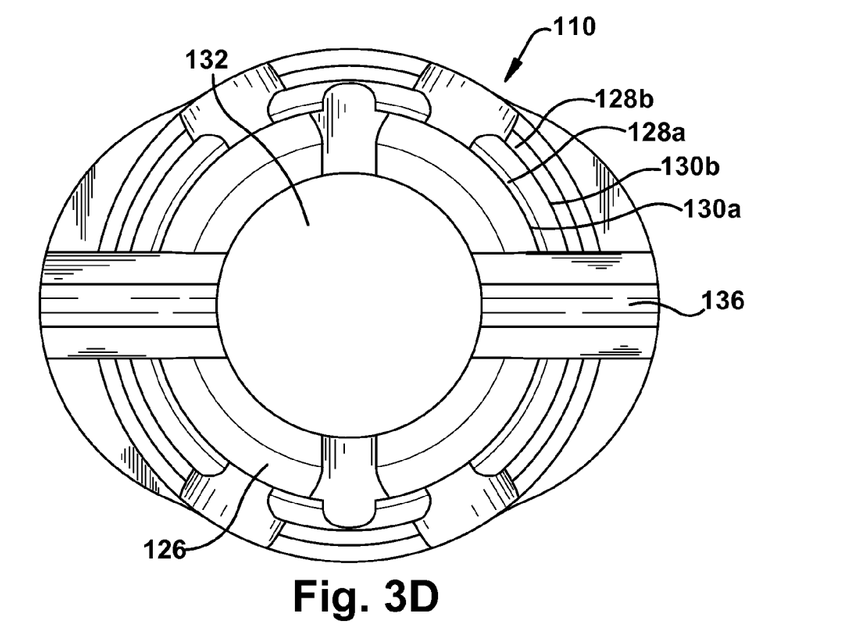

The rod seat 110, and consequently the separate pieces 110a and 110b may include one or more internal steps, each having an edge configured to engage the fixation device 104. As shown, the rod seat 110 includes two internal steps 128a and 128b. Each of the internal steps 128a and 128b may be continuous or noncontinuous around the perimeter of the rod seat 110. FIGS. 3C-D illustrate an exemplary configuration having noncontinuous steps 128a and 128b. In addition, internal step 128b may define an opening in the bottom portion 125 of the rod seat 110. Each of the internal steps 128a and 128b may have an edge, 130a and 130b respectively, that is brought into contact with the fixation device 104, and more specifically, with the top portion 146 of the head 140 of the fixation device 104. At the same time, the lip 117 may be brought into contact with the bottom portion 148 of the head 140 of the fixation device 104. Thus, the position of the rod 106 is fixed with respect to the position of the fixation device 104. In addition, the ability of the locking mechanism 100 to maintain the rod 106 and fixation mechanism 104 in locked positions may be enhanced following the separation of the rod seat 110 and further urging the rod 106 toward the bottom portion 114 of the body 102.

In one embodiment, the edges 130a and 130b of the internal steps 128a and 128b of each of the separate pieces 110a and 110b of the rod seat 110 apply force to the top portion 146 of the head 140 of the fixation device 104 in a direction that is not parallel to the central axis 101 of the body 102. For example, the edges 130a and 130b may exert force F on the fixation device 104 at an angle θ offset from the central axis 101 of the body 102. The force applied by edge 130a of piece 110a and the force applied by the edge 130a of piece 110b may be offset from the central axis 101 by approximately the same angle, such as angle θ. Similarly, the force applied by edge 130b of piece 110a and the force applied by the edge 130b of piece 110b may be offset from the central axis 101 by approximately the same angle. Moreover, the two pieces 110a and 110b of the rod seat 110 may each be configured to exert force on the fixation device 104 directed at an angle θ that is off axis from the central axis 101 of the body 102 by up to approximately 45 degrees. In one embodiment, the angle θ ranges from about 10 degrees to about 30 degrees.

Figure 4:
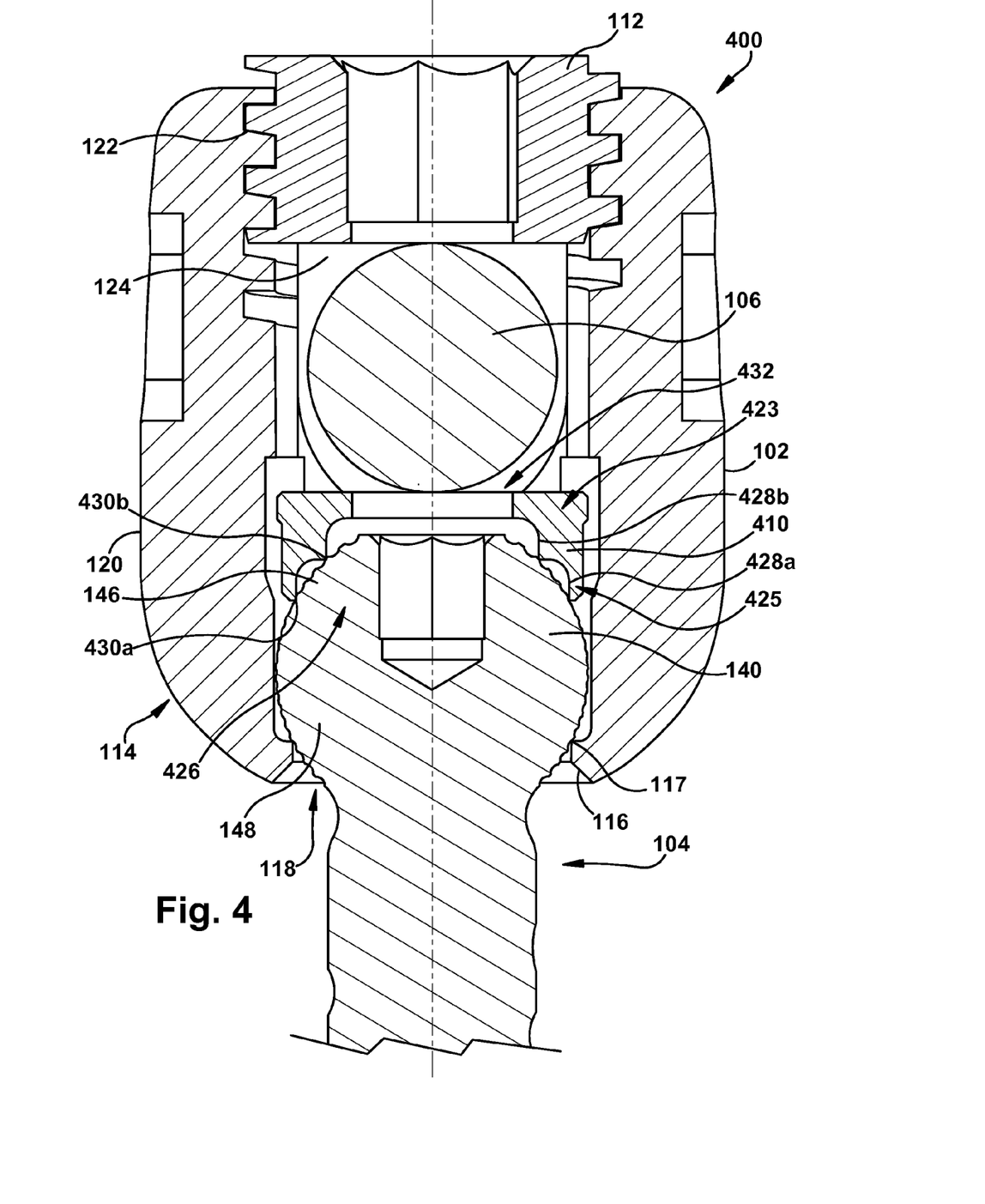
FIG. 4 is a cross-sectional view of a locking mechanism having a washer between the rod and fixation device in a locked position.

Turning next to FIG. 4, illustrated is a cross-sectional view of another locking mechanism 400 in a locked position. The locking mechanism 400 is configured to engage and lock the position of a fixation device 104 with respect to the position of a rod 106. The locking mechanism 400 includes a body 102, a washer 410 and a locking element 112.

The fixation device 104 is preferably inserted through the top of the body 102 prior to insertion of the washer 410 and rod 106. The washer 410 is then preferably inserted through the top of the body 102 so that the bottom portion 425 of the washer 410 is positioned for interaction with the top portion 146 of the head 140 of the fixation device 104. As will be understood by those skilled in the art, the washer 410 may be wider than the opening in the top of the body 102. Thus, to insert the washer 410, a tool may be used to increase the size of the opening in the top of the body 102. The rod 106 is then inserted into the body 102. The washer 110 is preferably inserted into the body 102 prior to insertion of the rod 106 such that the washer 110 is eventually positioned between the rod 106 and the head 140 of the fixation device 104.

The washer 410 may be made from a variety of materials known in the art and preferably is made from a biocompatible material when the locking mechanism 100 is used for bone fixation. Such materials include, but are not limited to, titanium, titanium alloys (e.g. titanium/aluminum/vanadium (Ti/Al/V) alloys), cobalt-chromium alloys, stainless steel, ceramics (alumina ceramic, zirconia ceramic, yttria zirconia ceramic, etc.), high strength polymers (e.g. PEEK, PEKK, etc.), pyrolytic carbon, tantalum, carbon composite materials and combinations thereof, which may include mechanically compatible mixtures of the above materials. Such materials are commonly used in bone fixation and the like. Preferably, the materials are rigid and in one embodiment, the washer 410 is made from Ti/Al/V alloys, such as Ti/6Al/4V ELI.

The washer 410 may be configured to at least partially surround the head 140 of the fixation device 104. The diameter of the head 140 is preferably larger than the hole 118 so that the head 140 cannot be removed through the hole 118 in the bottom 114 of the body 102. The washer 410 may also include a top hole 132 and a bottom hole 126 to provide access to the head 140 of the fixation device 104 from the top of the body 102. Thus, a driver or similar device may be used to engage the head 140 of the fixation device 104 via the washer 110. In this manner, the fixation device 104 can be tightened using a driver or the like without permanently fixing the position of the fixation device 104 with respect to the body 102 and rod 106.

Figure 5A:
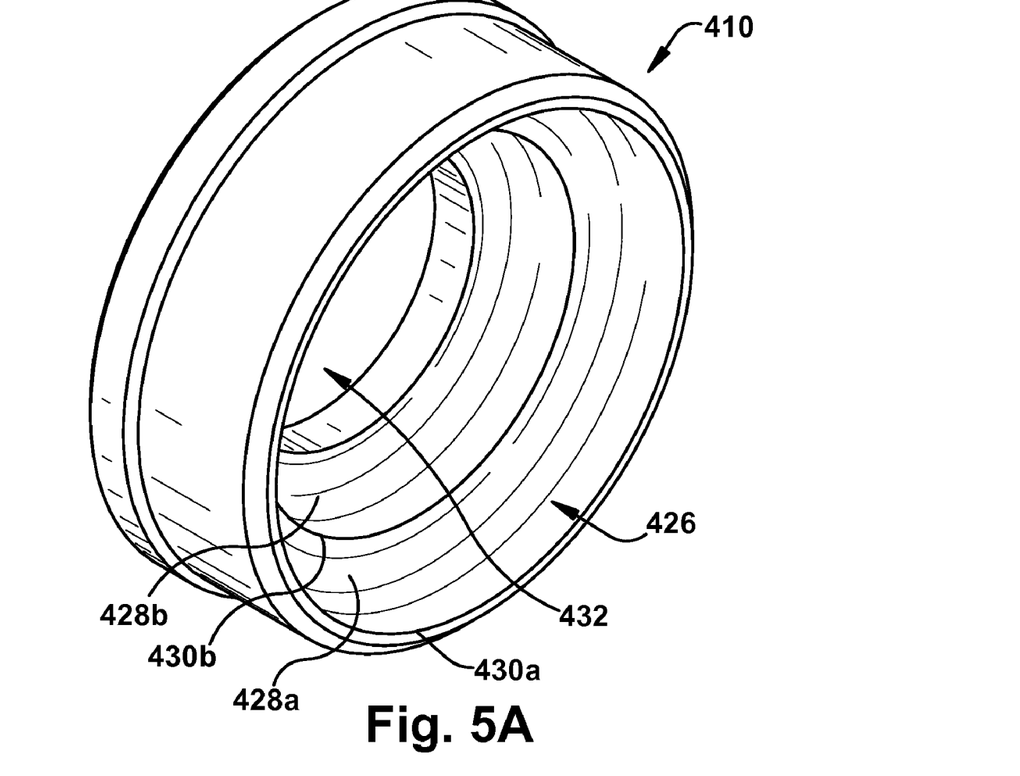
FIGS. 5A-B are top and bottom perspective views of the washer of FIG. 4.
Figure 5B:
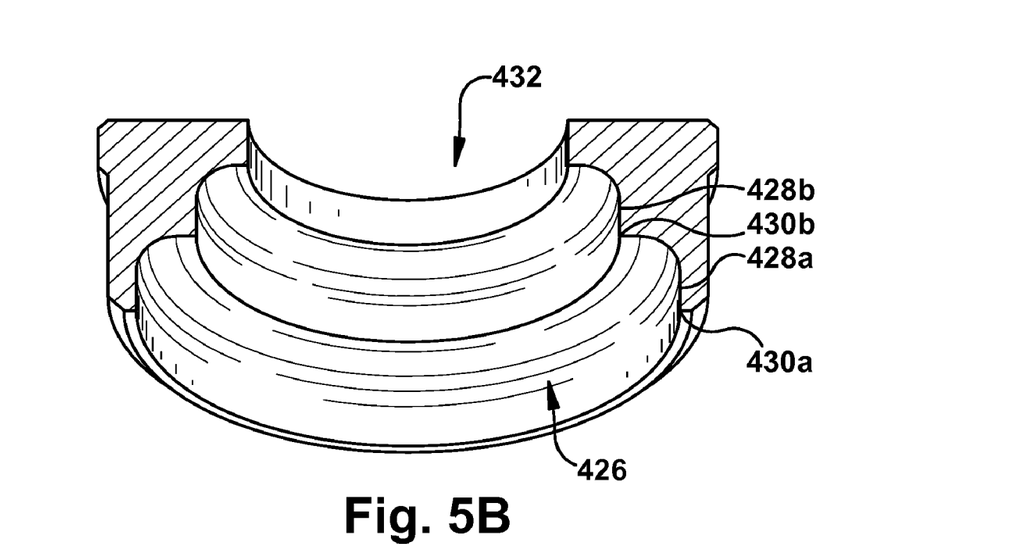

Turning next to FIGS. 5A-B, full and cross-sectional perspective views of an embodiment of the washer of FIG. 4 are illustrated. The washer 410 includes a bottom hole 126 that is sized to accept part of the top portion 146 of the head 140 of the fixation device 104. The washer 410 may be generally circular disc shaped such that cross sections of the washer 110 are generally circular.

The washer 110 also preferably includes at least two internal steps 428a and 428b. The internal steps 428a and 428b each have an edge 430a and 430b, respectively for contacting the surface of the top portion 146 of the head 140 of the fixation mechanism 104 during engagement. Each of the internal steps 428a and 428b may be continuous or noncontinuous around the perimeter of the rod seat 110, such as shown in FIGS. 3C-D illustrating the rod seat 110. In addition, the edge 430a may define the opening 426 of the washer 410 and one or both of edges 430a and 430b may define circular openings.

In use, the locking element 112 is engaged is tightened down to apply force to the rod 106 in order to engage and lock the rod 106 and fixation device 104. More specifically, the tightening of the locking element 112 causes linear compression of the rod 106 onto the washer 110, which in turn forces the fixation device 104 toward the bottom portion 114 of the body 102. As the rod 106 is forced downward, such as by tightening of the locking element 112, the washer 110 and head 140 combination is forced downward into the socket 116, which preferably includes a lip 117. As shown, the lip 117 is tapered and preferably has an edge. Accordingly, the lower portion 148 of the head 140 is caused to contact the lip 117, and preferably, the edge of the lip, thereby preventing the head 140 of the fixation device 104 from moving further through the hole 118. As the locking element 112 is further tightened, the rod 106 is forced more tightly against the top of the washer 110 and the edges 430a and 430b are brought into tighter contact with the top portion 146 of the head 140 of the fixation device while the lip 117 is brought into tighter contact with the bottom portion 148 of the head 140 of the fixation device 104. Thus, the position of the rod 106 is fixed with respect to the position of the fixation device 104.

Figure 6:
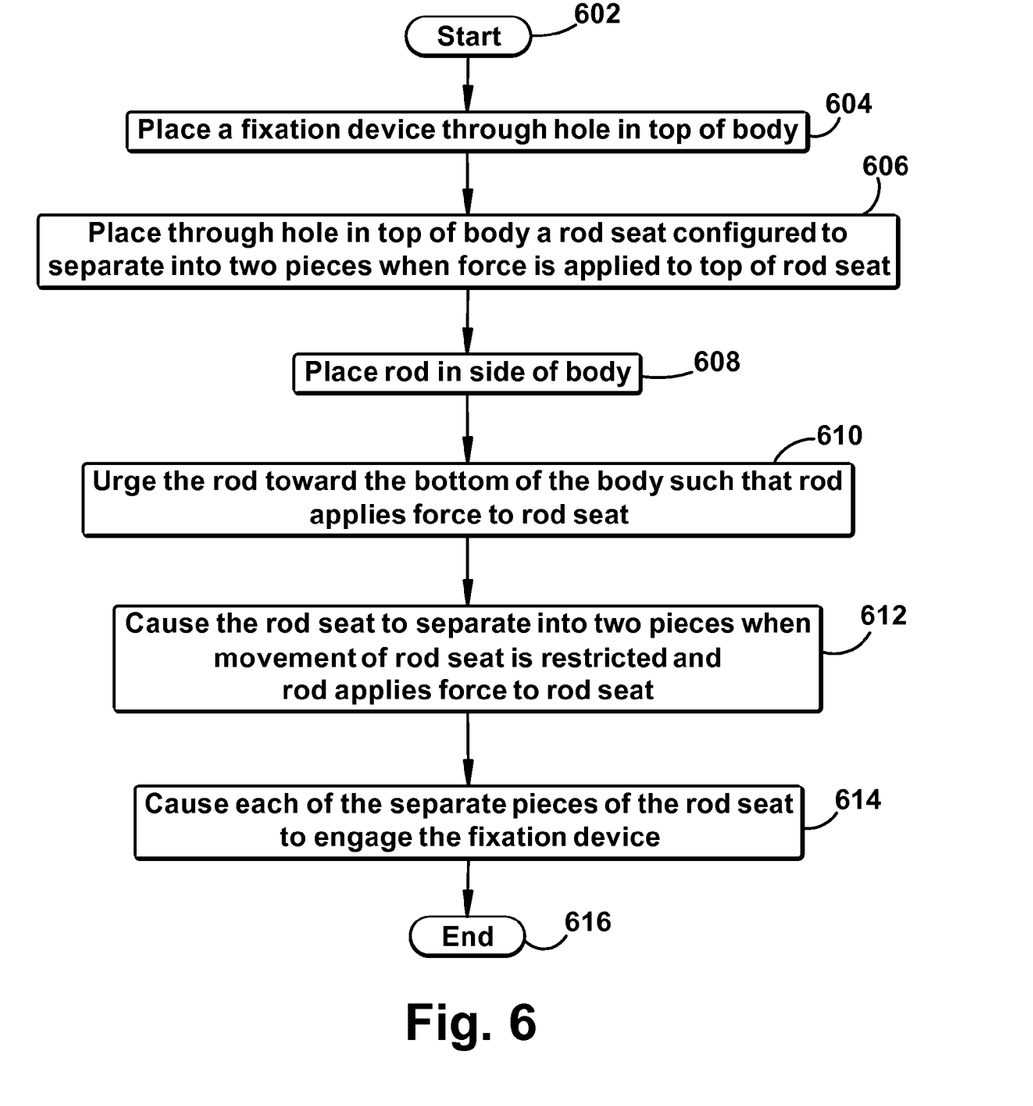
FIG. 6 is a flow chart illustrating a novel method of fixing the position of a rod with respect to a fixation device.

Turning next to FIG. 6, a flow chart illustrates a novel method of fixing the position of a rod with respect to a fixation device. Flow begins at start block 602 from which progression continues to process block 604 wherein a fixation device, such as fixation device 104, is placed through a hole in a top portion of a body, such as body 102, of a locking mechanism. Progression then flows to process block 606 wherein a rod seat, such as the rod seat 110, is placed through the hole in the top of the body. The rod seat is configured to separate into two pieces when force is applied to the top portion of the rod seat and movement of the rod seat is restricted. Progression then continues to process block 608 wherein a rod, such as the rod 106, is inserted into the side of the body such that the rod and the fixation device are on opposite sides of the rod seat. Flow then progresses to process block 610 wherein the rod is urged toward the bottom portion of the body. Progression then flows to process block 612 wherein the rod applies force to top portion of the rod seat and the fixation device restricts movement of the rod seat toward the bottom portion of the body, thereby causing the rod seat to separate into two pieces. Flow then continues to process block 614 wherein each of the separate pieces of the rod seat engage the fixation device. Flow then progresses to termination block 616.

Figure 7:
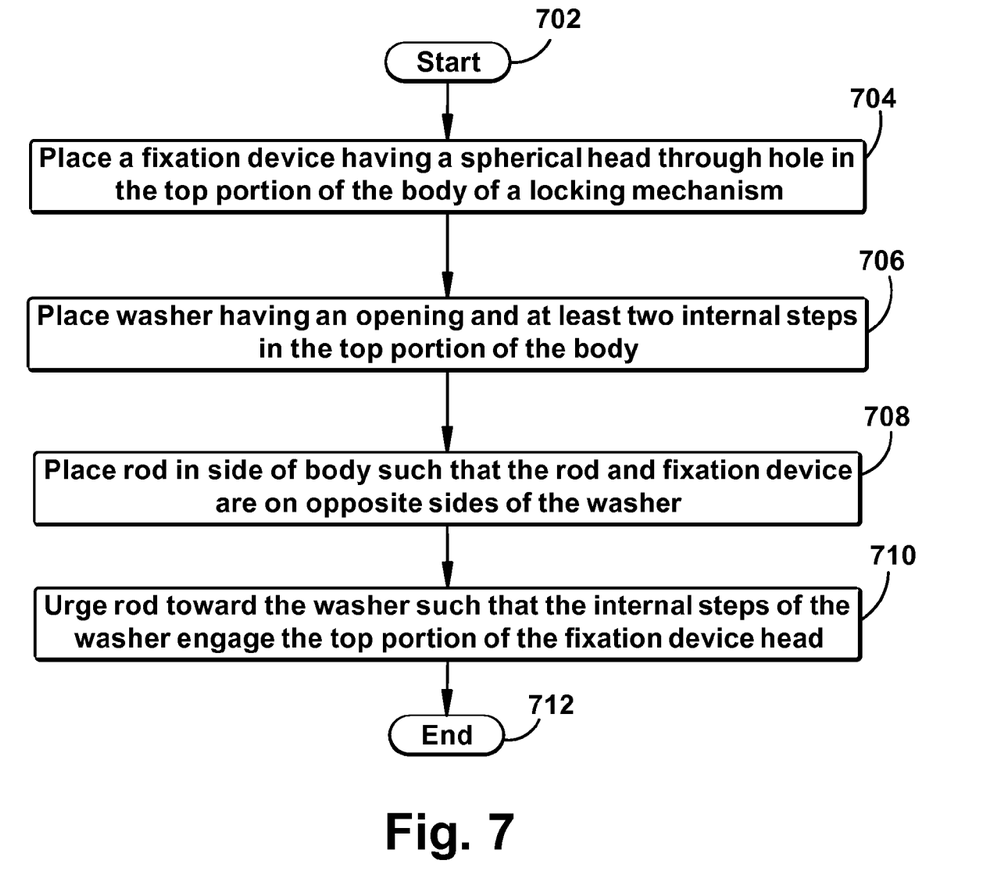
FIG. 7 is a flow chart illustrating another novel method of fixing the position of a rod with respect to a fixation device.

Turning next to FIG. 7, a flow chart illustrates an additional novel method of fixing the position of a rod with respect to a fixation device. Flow begins at start block 702 from which progression continues to process block 704 wherein a fixation device having a generally spherical head, such as fixation device 104, is placed through a hole in a top portion of a body, such as body 102, of a locking mechanism. Progression then flows to process block 706 wherein a washer having at least two internal steps, such as the washer 410, is placed through the hole in the top of the body. Progression then continues to process block 708 wherein a rod, such as the rod 106, is inserted into the side of the body such that the rod and the head of the fixation device are on opposite sides of the washer. Flow then progresses to process block 710 wherein the rod is urged toward the bottom portion of the body such that the internal steps of the washer engage the head of the fixation device. Flow then progresses to termination block 712.

While the present invention has been described in association with exemplary embodiments, the described embodiments are to be considered in all respects as illustrative and not restrictive. Such other features, aspects, variations, modifications, and substitution of equivalents may be made without departing from the spirit and scope of this invention which is intended to be limited only by the scope of the following claims. Also, it will be appreciated that features and parts illustrated in one embodiment may be used, or may be applicable, in the same or in a similar way in other embodiments.

Moreover, any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, it is intended that values such as 15 to 85, 22 to 68, 43 to 51, 30 to 32 and the like, are expressly enumerated in this specification. These are only examples of what is specifically intended and all possible combinations of numerical values between the lowest value and the highest value enumerated are to be considered to be expressly stated in this application in a similar manner.

What is claimed is:

1. A method for locking the relative positions of a fixation device and a rod comprising:
   placing a fixation device through a hole in the top of a body of the locking mechanism;
   placing a rod seat having a top portion and a bottom portion through the hole in the top portion of a body of a locking mechanism, wherein the rod seat is configured to separate into two pieces when force is applied to the top portion of the rod seat and movement of the rod seat is restricted;
   placing a rod in a side portion of the body such that the rod and the fixation device are on opposite sides of the rod seat; and
   urging the rod toward the bottom of the body such that the rod applies force to the top portion of the rod seat and the fixation device restricts movement of the rod seat toward the bottom of the body, thereby causing the rod seat to separate into two pieces;
   wherein each of the two pieces engage part of the fixation device.

2. The method of claim 1 further comprising further urging the rod toward the bottom of the body following the separation of the rod seat into two pieces.

3. The method of claim 2 wherein further urging the rod increases engagement between the pieces of the rod seat and the fixation device.

4. The method of claim 2 wherein the ability of the locking mechanism to maintain the rod and fixation mechanism in locked positions is enhanced following the separation of the rod seat and further urging of the rod toward the bottom of the body.

5. The method of claim 1 wherein urging the rod toward the bottom of the body comprises engaging a locking element on the side of the rod opposite the rod seat.

6. The locking mechanism of claim 1 wherein urging the rod toward the bottom of the body comprises exerting from approximately 50 lbs to approximately 2500 lbs of force on the rod.

7. The method of claim 1 wherein at least one lip at a bottom portion of the body restricts the movement of the fixation device toward the bottom of the body, thereby restricting the movement of the rod seat toward the bottom of the body during the application of force by the rod to the top portion of the rod seat.

8. The method of claim 1 wherein the top portion of the rod seat comprises a taper and wherein urging the rod toward the bottom of the body comprises causing the taper to widen.

9. The method of claim 1 wherein the rod seat separates along a central axis of the rod seat that is approximately parallel to a major axis of the rod.

* * * * *